US010213574B2

(12) United States Patent
Rowland et al.

(10) Patent No.: US 10,213,574 B2
(45) Date of Patent: Feb. 26, 2019

(54) INHALER DEVICE FOR INHALABLE LIQUIDS (71) Applicant: Medical Developments International Limited, Scoresby (AU)

(72) Inventors: Greg Rowland, Scoresby (AU); Edward Linacre, Abbotsford (AU); Glenn Gilbert, Scoresby (AU); Viktor Legin, Abbotsford (AU)

(*) Notice: Subject to any disclaimer, the term of this patent is extended or adjusted under 35 U.S.C. 154(b) by 0 days.

(21) Appl. No.: 15/745,877

(22) PCT Filed: Jul. 19, 2016

(86) PCT No.: PCT/AU2016/050638
§ 371 (c)(1),
(2) Date: Jan. 18, 2018

(87) PCT Pub. No.: WO2017/011867
PCT Pub. Date: Jan. 26, 2017

(65) Prior Publication Data
US 2018/0214661 A1    Aug. 2, 2018

(30) Foreign Application Priority Data

Jul. 20, 2015 (AU) ................ 2015902868
Jul. 20, 2015 (AU) ................ 2015902881

(51) Int. Cl.
*A61M 16/18* (2006.01)
*A61M 16/10* (2006.01)
(Continued)

(52) U.S. Cl.
CPC ............ *A61M 16/18* (2013.01); *A61M 11/04* (2013.01); *A61M 15/00* (2013.01);
(Continued)

(58) Field of Classification Search
CPC ............. A61M 15/00; A61M 15/0063; A61M 15/002; A61M 15/06; A61M 11/00;
(Continued)

(56) References Cited

U.S. PATENT DOCUMENTS 3,565,071 A * 2/1971 Cobb .................. A61M 15/00
                                                    128/203.24
6,871,647 B2   3/2005 Allan et al.
(Continued)

FOREIGN PATENT DOCUMENTS

WO    2009102276 A1    8/2009
WO    2010039202 A2    4/2010
WO    2012010878 A1    1/2012

OTHER PUBLICATIONS

International Search Report and Written Opinion Issued in PCT Application No. PCT/AU2016/050638, dated Oct. 12, 2016.

*Primary Examiner* — Colin W Stuart
(74) *Attorney, Agent, or Firm* — Westman, Champlin & Koehler, P.A.

(57) ABSTRACT

The present invention provides a new inhaler device for the storage and administration of inhalable liquids to a patient, such as halogenated volatile liquids, particularly methoxyflurane for use as an analgesic, the device having one or more advantages or improvements over known inhalers.

19 Claims, 6 Drawing Sheets (51) Int. Cl.
*A61M 15/00* (2006.01)
*A61M 11/04* (2006.01)
*A61M 16/01* (2006.01)

(52) U.S. Cl.
CPC ...... *A61M 15/002* (2014.02); *A61M 15/0035* (2014.02); *A61M 15/0063* (2014.02); *A61M 16/10* (2013.01); *A61M 16/104* (2013.01); *A61M 16/183* (2013.01); *A61M 16/01* (2013.01)

(58) Field of Classification Search
CPC ...... A61M 11/04; A61M 16/00; A61M 16/10; A61M 16/104; A61M 16/18; A61M 16/183; A61M 16/186; A61M 16/01
USPC .......................... 128/200.24, 202.21, 203.12
See application file for complete search history.

(56) References Cited

U.S. PATENT DOCUMENTS

2011/0290267 A1* 12/2011 Yamada ................ A24F 47/002
131/329
2015/0237913 A1* 8/2015 Suzuki .................. A24F 47/004
131/329

* cited by examiner

INHALER DEVICE FOR INHALABLE LIQUIDS

FIELD

The present invention relates to an inhaler device for inhalable liquids, in particular for the storage and/or administration of inhalable volatile liquids such as halogenated volatile liquids, to a patient.

BACKGROUND

The storage and administration of inhalable liquids to patients that comprise active agents, or that are themselves the active agent, commonly presents challenges. Due to patient preference and ease of self-administration or administration in a hospital setting or other settings as required, active agents such as therapeutic agents or pharmaceutical agents, are often formulated for oral delivery in the form of tablets and capsules, nasal delivery in the form of sprays and liquid formulations for intravenous delivery.

Where it is advantageous to administer active agents to a patient's lungs, for example to treat or alleviate respiratory diseases, the active agent may be administered by the oral inhalation route, alone or in combination with the intranasal route. Suitable inhaler devices may include, for example, metered dose inhalers and dry powder inhalers. These types of oral inhalation devices typically require pressurised means to deliver the active agent to the desired site of action in the lungs. In addition, liquids that contain active agents or that are themselves the active agent usually require transformation into an inhalable, respirational, form at the point of administration to be suitable for delivery by the inhalation route. Transforming a liquid into an inhalable form, such as by nebulisation or aerosolizing into respirational sized droplets or heating to form a vapour, requires delivery devices to include moving, mechanical, heating and/or electrical means which adds to the complexity of the design, manufacturing and end user costs, operability and/or patient use.

The use of volatile liquids as active agents or comprising active agents is known. One such example is halogenated volatile liquids. Halogenated volatile liquids have been described as useful for inducing and/or maintaining anaesthesia (including amnesia, muscle paralysis, and/or sedation) and/or analgesia and may therefore be useful as anaesthetics and/or analgesics. The anaesthetic properties of fluorinated compounds have been known since at least 1946 (Robbins, B. H. *J Pharmacol Exp Ther* (1946) 86: 197-204). This was followed by the introduction of fluoroxene, halothane and methoxyflurane into clinical use in the 1950s and the subsequent development of enflurane, isoflurane, sevoflurane and desflurane which are in clinical use in some countries today (Terrell, R. C. *Anesthesiology* (2008) 108 (3): 531-3).

Halogenated volatile liquids, when used for general anaesthesia, may be delivered to a patient under positive pressure via a delivery system that includes a vaporizer and a flow of breathable carrier gas. More recently, halogenated volatile liquids have been formulated for use in local or regional anaesthesia and delivery via non-inhalation routes. Examples include formulation as: microdroplets for intradermal or intravenous injection (e.g. U.S. Pat. No. 4,725, 442); aqueous solutions for intrathecal or epidural delivery (e.g. WO2008/036858); swab, droplets, spray or aerosol for transmucosal delivery (e.g. WO2010/025505); aqueous based solutions comprising an extractive solvent in an amount effective to reduce the volatility, vaporisation or evaporation of the volatile anaesthetic for transdermal, topical, mucosal, buccal, rectal, vaginal, intramuscular, subcutaneous, perineural infiltration, intrathecal or epidural delivery (e.g. WO2009/094460, WO2009/094459); compositions suitable for formulation into a medical patch (e.g. WO2014/143964); compositions suitable for formulation as a solution, suspension, cream, paste, oil, lotion, gel, foam, hydrogel, ointment, liposome, emulsion, liquid crystal emulsion and nanoemulsions for topical, intrathecal, epidural, transdermal, topical, oral, intra-articular, mucosal, buccal, rectal, vaginal, intramuscular, intravesical and subcutaneous delivery (e.g. WO2008/070490, WO2009/094460, WO2010/129686); and stable and injectable liquid formulations (WO2013/016511).

The main consideration(s) for the safe storage and handling of volatile liquids commonly include vapour pressure build up, the robustness of the container and the integrity of the container seal(s). The chemical nature of the volatile liquid may also be important if the active agent is capable of permeating, solubilizing or otherwise reacting with the container material(s) upon storage. A number of storage containers for halogenated volatile liquids have been described including: rigid polymeric containers as a replacement for glass vials, such as capped bottles large tanks, shipping containers (e.g. WO1999/034762, WO2012/116187); rigid polymeric bottles fitted with a gasketless valve assembly and pliable containers with a threaded spout for fluid connection to deliver liquid anaesthetics to an anaesthetic machine or vaporizer (e.g. WO2010/135436, WO2013/106608, WO2013/149263, WO2015/034978); a container with a capped membrane for delivering a stored liquid anaesthetic to a vaporizer via a slotted tube (WO2009/117529); and rigid polymeric and aluminium containers optionally coated with materials to impart or enhance vapour barrier characteristics or container inertness (e.g. WO2002/022195, WO2003/032890, WO2010/129796).

Despite the various advances in formulating volatile liquids in non-inhalable forms, such as the halogenated volatile liquids, as well as containers to store them, there still remains a need for inhalable forms of volatile liquids and devices to store and/or administer them to patients.

Attempts to design new inhalers for inhalable medicines in general are ongoing. For example, WO2008/040062 describes a diverse number of inhaler device concepts that depend on complex constructions and moving parts for storing and/or delivering inhalable liquids and powdered solids into a user's mouth or nose. The various devices described are adapted to hold one or two medicament containers in the form of pressurised canisters, ampoules, vials and plungers. The devices are described as being activated by sliding an outer wall of the device in relation to an inner wall of the device to deliver the liquid medication from a medication container. In a number of embodiments, the device includes a moveable mouthpiece which deploys in order to open the air pathway. The device is also described as including one or more one-way valves to provide a unidirectional air flow for one or both inhaled air and exhaled air (a series of one-way valves to direct the flow of inhaled and exhaled air has also been generally described in WO2007/033400 which is an incorporation by reference of the device described in WO1997/003711).

When required for use, the devices of WO2008/040062 are claimed as being capable of releasing the medication by punching means namely two punches to perforate the two frangible ends respectively of a medication container having frangible ends, although various other means are generally described including: pressurised means (e.g. by a pressurised canister); frangible means (e.g. by rupturing an ampoule with a striker or by punching a frangible membrane or seal of a vial with punch means); crushable means (e.g. by crushing a vial with a plunger); dislodging means (e.g. by dislodging an unscrewed cap from a vial); and plunging means (e.g. by plunging the medication from the plunger barrel).

However, inhalable liquids such as halogenated volatile liquids require an effective air chamber into which the vapour may evaporate and allow an effective airflow through the air/vapour chamber for delivery to a patient. Accordingly, embodiments such as those described in, for example, FIGS. 48A, 48B, 48C, 49A, 49B, 50A, 50B, 51A, 51B, 56A, 56B, 57, 58A, 58B, 58C and 58D of WO2008/040062, would not be expected to work in practice as the evaporative means (or wick) is prevented from being effectively exposed to the released liquid by the walls of the liquid storage container itself.

The present invention provides a new inhaler device for the storage and administration of inhalable liquids to a patient offering one or more advantages or improvements over known inhalers, particularly inhalers for the delivery of halogenated volatile liquids such as methoxyflurane for use as an analgesic. The device is capable of storing and administering an inhalable liquid with a minimum of two manufactured parts (excluding the passive evaporation support material pre-loaded with the inhalable liquid). The device offers an easy to use, pre-loaded (i.e. primed for use), readily portable and low-cost manufactured device which may also provide further reductions in shipping, storage and disposal costs as well as material wastage, by avoiding the need to store the liquid in a separately manufactured container.

SUMMARY

According to a first aspect of the invention there is provided an inhaler device for the storage and delivery of an inhalable liquid to a patient, said device comprising a puck-shaped body wherein the puck-shaped body comprises:
(1) A receptacle comprising a passive evaporation support material pre-loaded with the inhalable liquid;
(2) A receptacle lid;
(3) At least one air inlet opening; and
(4) At least one vapour inhalation opening;
wherein the air inlet and vapour inhalation openings are in a closed position when the receptacle lid is closed for storing the inhalable liquid and further wherein as the inhalable liquid forms a vapour upon storage, the puck-shaped body forms a vapour chamber such that the stored vapour is available for direct administration to a patient when the lid is opened to provide an air/vapour pathway through the vapour chamber via the air inlet and vapour inhalation openings.

According to a second aspect of the invention there is provided an inhaler device for the storage and delivery of an inhalable liquid to a patient, said device comprising a puck-shaped body, said puck-shaped body consisting only of:
(1) A receptacle comprising a passive evaporation support material pre-loaded with the inhalable liquid;
(2) A receptacle lid;
(3) At least one air inlet opening; and
(4) At least one vapour inhalation opening;
wherein the air inlet and vapour inhalation openings are in a closed position when the receptacle lid is closed for storing the inhalable liquid and further wherein as the inhalable liquid forms a vapour upon storage, the puck-shaped body forms a vapour chamber such that the stored vapour is available for direct administration to a patient when the lid is opened to provide an air/vapour pathway through the vapour chamber via the air inlet and vapour inhalation openings.

In one embodiment according to the first and second aspects, the receptacle lid is rotatably opened.

In one embodiment according to the first and second aspects, the air inlet opening and the vapour inhalation opening are formed in the receptacle lid. In a further embodiment, the receptacle lid comprises an integrally formed mouthpiece for delivery of the vapour via the vapour inhalation opening.

In one embodiment, the inhalable liquid is a halogenated volatile liquid. In a further embodiment the halogenated volatile liquid is selected from the group consisting of halothane (2-bromo-2-chloro-1,1,1-trifluoroethane), sevoflurane (fluoromethyl-2,2,2-trifluoro-1-(trifluromethyl) ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether). In one embodiment, the inhalable liquid is methoxyflurane for use as an analgesic.

BRIEF DESCRIPTION OF THE FIGURES

FIG. 2 shows an inhaler device according to an embodiment of the invention (FIG. 2A) and a broken line drawing view (FIG. 2B).

FIG. 4 shows further views of the inhaler device of FIG. 2A, specifically a rear end view showing an air inlet opening in an opened position (FIG. 4A), a front end view showing a vapour inhalation opening in an opened position (FIG. 4B) and cross-sectional view to give a side perspective of the device along line A-A of FIG. 4B (FIG. 4C).

FIG. 5 shows a top view of the inhaler device of FIG. 2A (FIG. 5A) and a side view of the device in use upon inhalation by a patient (FIG. 5B).

DETAILED DESCRIPTION

Inhaler devices that are useful for administering inhalable liquids may be generally considered to operate by either passive or active means in order to deliver the active agent(s) to a patient. Inhaler devices with active means may include pressurized, moving, mechanical, heating and/or electrical means to, for example, nebulise, vaporize and/or generally deliver the active agent(s). In contrast, inhaler devices with passive means rely solely on the vaporisation or evaporation of the active agent(s) at ambient conditions and respiration of the patient to deliver the active agent(s).

The Analgizer™ inhaler device (Abbott Laboratories Corporation) is an example of a device that operates by passive means to deliver an inhalable liquid. According to the USPTO TESS database, the Analgizer™ was a registered, now lapsed, trademark in respect of an inhaler for the supervised self-administration of inhalation anaesthesia and was first used in 1968. The Analgizer™ was a very simple device that consisted of a white cylindrical polyethylene open-ended tube having a mouthpiece and an absorbent wick of polypropylene which was tightly rolled into a 'Swiss-roll' shape, i.e. cross-sectional view. The inhalation anaesthetic, methoxyflurane (15 mL), was poured into the open ended base of the inhaler and onto the tightly wound wick, just prior to use. A patient was then able to self-administer the liquid anaesthetic by inhaling through the mouthpiece.

The Green Whistle™ inhaler device (Medical Developments International Limited) was subsequently developed during the 1990s and has since been used in Australia for the delivery of Penthrox®/™ (methoxyflurane) as an analgesic (1.5 mL or 3 mL, storage brown glass vial container with screw cap). Although similar in its simplicity of design to the Analgizer™, the Green Whistle™ device includes certain functional improvements such as the inclusion of a one-way valve at the base end to prevent drug vapour loss from the device upon patient exhalation and an activated carbon ('AC') chamber designed to be externally fit into a dilution hole in the mouth piece to filter exhaled drug vapours. Additional design modifications to the base end included the introduction of cap lugs to assist removal of the cap from the glass vial used to store the drug dose to be delivered, a dome to facilitate the spread of the poured liquid onto the 'S-shaped' wick (i.e. cross-sectional view) or, in the alternative to a dome, an inlet nipple to allow for the attachment of a breathable gas line to direct the gas through the device. The Green Whistle™ device is designed for single patient use.

Methoxyflurane (Penthrox®/™, Medical Developments International Limited) offers a non-narcotic, i.e. non-opioid analgesic alternative to common analgesics such as morphine and fentanyl. Methoxyflurane also presents an alternative to analgesics which are administered in oral tablet form or intraveneously to a patient and may therefore be particularly useful when rapid pain relief is required in clinical, surgical (e.g. pre- and post-operative) and/or emergency settings (e.g. emergency department and triage management as well as by first-responders such as paramedics and search and rescue teams). However, the Green Whistle™ device is currently the only device that is commercially available to administer methoxyflurane. According to the device's instructions for use, the administrator is required to hold the methoxyflurane bottle upright to use the base of the inhaler to loosen the bottle cap and then to remove the cap by hand before tilting the inhaler to a 45° angle and pouring the contents of the bottle into the base while rotating the device. An AC-chamber may be optionally fitted externally to the device either beforehand or afterwards. While the device is effective, the number of steps and separate components may present handling difficulties for the administrator or self-administrator, for example, in high-stress and/or emergency settings.

The present invention provides a new inhaler device for the storage and administration of inhalable liquids to a patient, such as halogenated volatile liquids, particularly methoxyflurane for use as an analgesic, the device having one or more advantages or improvements over known inhalers.

Definitions

Unless otherwise herein defined, the following terms will be understood to have the general meanings which follow.

'Active agent' refers to therapeutic agents and non-therapeutic agents and compounds, formulations and compositions comprising them.

'Alleviate', 'Alleviation' and variations thereof refers to relieving, lessening, reducing, ameliorating or an improvement in the symptom(s) and/or underlying cause(s) of a condition and/or disease in a patient.

'Delivery dose' refers to the dose of inhalable liquid or active agent for administration to a patient.

'Filter', 'Filtering' and variations thereof refers to the ability of a substance to absorb, adsorb, capture, trap, scavenge, scrub or partially or entirely remove the inhalable volatile liquid vapour from the exhaled breath of a patient upon exhalation.

'Halogenated volatile liquids' refers to volatile liquids which (i) comprise at least one halogen atom selected from the group consisting of a chlorine (CI), bromine (Br), fluorine (F) and iodine (I) atoms, or (ii) comprise an active agent which comprises at least one halogen atom selected from the group consisting of a chlorine (CI), bromine (Br), fluorine (F) and iodine (I) atoms. In some embodiments, halogenated, particularly fluorinated, hydrocarbons and halogenated, particularly fluorinated, ethers may be preferred. In some embodiments, halogenated ethers may be particularly preferred and include but are not limited to, halothane (2-bromo-2-chloro-1,1,1-trifluoroethane), sevoflurane (fluoromethyl-2,2,2-trifluoro-1-(trifluromethyl) ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether).

'Inhalable liquid' refers to liquids that comprise active agents or that are themselves the active agent and that are readily inhalable or capable of being or adapted to be inhaled by a patient. In some embodiments, inhalable volatile liquids, particularly halogenated volatile liquids are preferred.

'Inhalation', 'Inhalable' and variations thereof refers to the intake of, for example but not limited to air, breathable gases, inhalable liquids, by a patient and includes both oral and nasal inhalation. In some embodiments, oral inhalation is particularly preferred.

'Patient' refers to both human and veterinary patients. In some embodiments, human patients may be particularly preferred. Reference to a patient will therefore be understood to mean the person or animal to whom the inhalable liquid is administered to and in the case of human patients, will be understood to include administration by self-administration.

'Pharmaceutical agent' refers to a drug, or a compound, formulation or composition that comprises a drug, for the treatment of symptom(s) and/or underlying cause(s) of a condition and/or disease in a patient. The term pharmaceutical agent may be used interchangeably with therapeutic agent or active agent.

'Respiratory', 'Respirational' and variations thereof refers to the act of respiring, breathing, inhaling and exhaling, such as for example but not limited to air, breathable gases, inhalable liquids and active ingredients, by a patient.

'Room temperature' refers to ambient temperatures which may be, for example, between 10° C. to 40° C. but more typically between 15° C. to 30° C.

'Therapeutic agent' refers to an active agent, or a compound, formulation or composition (including biological compounds, formulations and compositions) that comprises an active agent, that is capable of treating a patient or offers a therapeutic or medical benefit to a patient or that has or that requires regulatory and/or marketing approval for therapeutic use in a patient. Therapeutic agents include pharmaceutical agents. In contrast, a 'Non-therapeutic agent' will be understood to mean an active agent which may not have or require regulatory and/or marketing approval for a therapeutic use such as, for example, smokeless tobacco products and electronic cigarettes, or does not have a recognised or identified therapeutic use but may be used by a patient for a non-therapeutic reason such as general health, wellbeing or physiological benefit such as, for example, nutraceutical products.

'Treat', 'Treatment' and variations thereof refers to the alleviation, modulation, regulation or halting of the symptom(s) and/or underlying cause(s) of a condition and/or disease in a patient. In some embodiments treatment may include preventative or prophylactic treatment.

'Volatile liquids' refers to substances that predominantly exist in a liquid form but readily form vapours, evaporate or vaporize such that they partially exist in a vapour form under ambient conditions for example, at room temperature and at normal atmospheric pressures.

EMBODIMENTS

Embodiments will now be described with reference to the non-limiting examples.

There is provided an inhaler device for the storage and delivery of an inhalable liquid to a patient, said device comprising a puck-shaped body wherein the puck-shaped body comprises:
(1) A receptacle comprising a passive evaporation support material pre-loaded with the inhalable liquid;
(2) A receptacle lid;
(3) At least one air inlet opening; and
(4) At least one vapour inhalation opening;
wherein the air inlet and vapour inhalation openings are in a closed position when the receptacle lid is closed for storing the inhalable liquid and further wherein as the inhalable liquid forms a vapour upon storage, the puck-shaped body forms a vapour chamber such that the stored vapour is available for direct administration to a patient when the lid is opened to provide an air/vapour pathway through the vapour chamber via the air inlet and vapour inhalation openings.

In one embodiment there is provided an inhaler device for the storage and delivery of an inhalable liquid to a patient, said device comprising a puck-shaped body, said puck-shaped body consisting only of:
(1) A receptacle comprising a passive evaporation support material pre-loaded with the inhalable liquid;
(2) A receptacle lid;
(3) At least one air inlet opening; and
(4) At least one vapour inhalation opening;
wherein the air inlet and vapour inhalation openings are in a closed position when the receptacle lid is closed for storing the inhalable liquid and further wherein as the inhalable liquid forms a vapour upon storage, the puck-shaped body forms a vapour chamber such that the stored vapour is available for direct administration to a patient when the lid is opened to provide an air/vapour pathway through the vapour chamber via the air inlet and vapour inhalation openings.

While the inhaler device is described as being 'puck-shaped' it will be understood that variations may be accommodated. For example, the receptacle lid may be curved e.g. domed, instead of flat or it may also adopt a different external shape by virtue of, for example, the addition of optional grips to assist the user with opening the lid. The puck-shaped body may also be elongated or truncated with reference to its height although in one embodiment, there is provided a truncated puck-shaped body having a flat top (i.e. top of receptacle lid) and flat bottom (i.e. bottom of receptacle) to provide a slim-line and readily stackable device for pocket-sized storage and portability.

When required for use, the air inlet opening(s) and vapour inhalation opening(s) are opened to enable the air to flow into the vapour chamber and across the surface(s) of the passive evaporation support material to deliver the vapour to the patient as the patient inhales.

The air inlet opening(s) and vapour inhalation opening(s) may be formed in the puck-shaped body in a number of ways to provide an air flow pathway through the vapour chamber. For example, the opening(s) may be formed by groove(s) or hole(s) in the receptacle or receptacle lid which may be exposed when the lid is opened or may be formed by groove(s) or hole(s) in the receptacle lid which partially or fully align with corresponding groove(s) or hole(s) in the receptacle when the lid is adjustably opened.

In one embodiment, the air inlet opening and the vapour inhalation opening are formed in the receptacle lid to provide an air flow pathway through the vapour chamber when the lid is opened to deliver the vapour to the user when the user inhales. In another embodiment, the air inlet opening and the vapour inhalation opening are formed in both the receptacle lid and the receptacle to provide an air flow pathway through the device when the lid is adjustably opened to adjustably control the airflow pathway by partially or fully aligning the opening(s) in the lid with the opening(s) in the receptacle to deliver the vapour to the user when the user inhales. In one embodiment, the receptacle lid comprises an integrally formed mouthpiece for delivery of the vapour via the vapour inhalation opening.

The receptacle lid may be opened, for example, by popping, upward pulling, twisting, turning, rotating or unscrewing the lid relative to the receptacle. In one embodiment the receptacle lid is rotatably opened. The receptacle lid may be detachably fastened to sealingly engage with the receptacle by, for example, a screw thread arrangement or a snap-fit joint arrangement. The air flow pathway may be adjustably controlled by the degree of popping, upward pulling, twisting, turning, rotating or unscrewing of the lid relative to the receptacle to provide partially opened or fully opened opening(s). The receptacle lid may also advantageously enable the device to be temporarily sealed by closing the lid to prevent excess vapour escaping through the opening(s) during intermittent use.

The receptacle lid may optionally comprise a wad insert to assist with sealing and resealing the device for storage mode. Accordingly, in one embodiment the receptacle lid optionally comprises a wad insert. The wad insert may comprise a compressible material and a vapour impermeable film or foil to assist with providing a tight seal when the receptacle lid is closed. Examples of compressible materials include but are not limited to polymeric foams or sponges such as LDPE.

Examples of vapour impermeable films include but are not limited to polymeric films, metal foils (such as, for example, aluminium, nickel and alloys thereof) and combinations, including co-extruded polymeric films and/or foils such as laminate films, thereof. In one embodiment the vapour impermeable film is a single layer selected from a polymeric film or a metal foil. In another embodiment the vapour impermeable film is a laminate film comprising two or more layers selected from a polymeric film, a metal foil and combinations, including co-extruded polymeric films and/or foils, thereof. The laminate film may comprise a weldable layer made from a suitable weldable foil or polymeric film such as, for example, LLDPE. A weldable layer may assist with sealing the layers of a laminate together and/or sealing a vapour impermeable film comprising a weldable layer to the device. Processes suitable for welding include thermal and ultrasonic welding.

In one embodiment the polymeric film has a MVTR of less than 100 g/m$^2$/24 h, preferably less than 50 g/m$^2$/24 h. In one embodiment the polymeric film comprises a polymer selected from the group consisting of a polyolefin, a polymeric phthalate, a fluorinated polymer, a polyester, a nylon, a polyvinyl, a polysulfone, a natural polymer and combinations, including co-extruded polymers thereof including biaxially orientated polymers such as, for example, biaxially orientated polypropylene (BOPP). In one embodiment the polymeric film comprises a polymer selected from the group consisting of PP, PE, LDPE, LLDPE, HDPE, BOPP, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof.

In one embodiment the vapour impermeable film comprises PET. In another embodiment the vapour impermeable film comprises PET and a metal foil layer, preferably an aluminium foil layer. In one embodiment the vapour impermeable film comprises metalised PET (Met PET).

The present device comprises a passive evaporation support material pre-loaded with the inhalable liquid to provide a portable, ready-to-use, all-in-one, drug storage and delivery device. In comparison to the prior inhaler devices for methoxyflurane, the present device provides easy administration, in particular self-administration when rapid pain relief is required, for example, in emergency, non-hospital, isolated, outdoor environment, sporting, humanitarian aid and/or field operation environments.

In one embodiment the passive evaporation support material is adapted to form a single longitudinal airflow/vapour pathway though the vapour chamber. In another embodiment, the passive evaporation support material is adapted to form at least two independent longitudinal airflow/vapour pathways though the vapour chamber. In yet another embodiment, the passive evaporation support material is adapted to form three or more independent longitudinal airflow/vapour pathways though the vapour chamber.

In one embodiment the passive evaporation support material is adapted to form a single longitudinal airflow/vapour pathway though the vapour chamber, the form being selected from the group consisting of a planar lining; a partial lining of the vapour chamber walls; and a full lining of the vapour chamber walls.

In another embodiment the passive evaporation support material is adapted to form at least two independent longitudinal airflow/vapour pathways, preferably three or more independent longitudinal airflow/vapour pathways, through the vapour chamber. Numerous examples of cross-sectional shapes which are capable of forming at least two, preferably three or more independent longitudinal airflow/vapour pathways may be envisaged, some of which follow. The two, preferably three or more independent longitudinal airflow/vapour pathways may be formed by the passive evaporation support material adopting a cross-sectional shape selected from a letter of the alphabet or a single digit number such as, for example although not limited to, an A-shape, B-shape, S-shape, Z-shape, figure-2, figure-5 and figure-8 which are capable of forming at least two independent airflow/vapour pathways, and a K-shape, M-shape, V-shape, W-shape, X-shape, Y-shape and figure-3 which are capable of forming three or more independent longitudinal airflow/vapour pathways through the vapour chamber.

In one embodiment the passive evaporation support material is adapted to provide three or more independent longitudinal airflow/vapour pathways. The pathways may be formed as independent conduits through the passive evaporation support material itself or the pathways may be formed by the evaporative means making contact with an internal surface of the vapour chamber. Accordingly, in one embodiment, the passive evaporation support material comprises three or more longitudinal conduits wherein the conduits are formed within the passive evaporation support material or are formed by the passive evaporation support material together with an internal surface of the vapour chamber or a combination thereof. Passive evaporation support material which are adapted to provide three or more independent longitudinal airflow/vapour pathways may be particularly suited to smaller sized devices.

The passive evaporation support material may be made from any material that is suitable for absorbing the inhalable liquid and passively releasing it as a vapour. Materials which have wicking properties are particularly preferred passive evaporation support material for use in the present device. Wicking properties will generally be understood to include the ability of a material to facilitate or enhance the rate of evaporation or vaporisation of a liquid from its surface by distributing the liquid, whether by drawing, spreading, pulling or otherwise, throughout the material from its initial point of contact and/or as it evaporates from an exposed surface area of the material. Accordingly, in one embodiment the passive evaporation support material is a wicking material. In one embodiment the wicking material is a wicking felt or a porous polymeric material. In a preferred embodiment the wicking material is a polypropylene wicking felt.

The present device is considered to be particularly useful for storing and administering a halogenated volatile liquid, particularly methoxyflurane for use as an analgesic. Accordingly, in one embodiment the inhalable liquid is a halogenated volatile liquid. In a further embodiment the halogenated volatile liquid is selected from the group consisting of halothane (2-bromo-2-chloro-1,1,1-trifluoroethane), sevoflurane (fluoromethyl-2,2,2-trifluoro-1-(trifluroromethyl) ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether). In a preferred embodiment, the inhalable liquid is methoxyflurane for use as an analgesic.

Suitable delivery doses of inhalable liquid for administration to a patient by the present device may be determined by reference to, for example, regulatory approved dosage amounts. Suitable delivery doses of methoxyflurane for use as an analgesic will typically be less than 15 mL and preferably less than 12 mL. In one embodiment the delivery dose is selected from the group consisting of 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL, 10 mL, 10.5 mL, 11 mL, 11.5 mL and 12 mL. In one embodiment the delivery dose of methoxyflurane for administration by the present device is selected from the group consisting of 1.5 mL, 3 mL and 6 mL.

The device may be made from various materials. However, suitable material(s) may be selected by considering whether they are chemically inert, stable and impervious with reference to the inhalable liquid to be stored and/or delivered. Material(s) may also be selected based on their suitability for medical device applications such as by reference to whether they meet approved standards for medical-grade human use by a regulatory authority like the FDA.

It is envisaged that the present device will be particularly useful for storing and administering halogenated volatile liquids. Accordingly, in one embodiment, the device is made from one or more materials that are compatible with the storage and delivery of halogenated volatile liquids to a patient, in particular methoxyflurane for use as an analgesic.

Examples of materials which may be suitable for making the present device include but are not limited to polymers (including homopolymers and heteropolymers i.e. co-polymers), composites (including nanocomposites), metals (including alloys thereof) and combinations thereof. In one embodiment, the device is made from polymers (including homopolymers and heteropolymers i.e. co-polymers), composites (including nanocomposites such as polymers in combination with clay), metals (including aluminium and alloys thereof) and combinations thereof. In a further embodiment, the device is optionally internally lined or coated with one or more material(s) selected from the group consisting polymers (including homopolymers and heteropolymers i.e. co-polymers), composites (including nanocomposites such as polymers in combination with clay), metals (including aluminium, nickel and alloys thereof), oxides (including aluminium oxides, silicon oxides), resins (including epoxyphenolic resins and ionomeric resins such as Surlyn®, trademark of DuPont), lacquers and enamels.

It is considered that one advantage of the present device is its relative simplicity and low cost to manufacture in addition to ease of operability in terms of the minimum number of individual components or parts required for the storage and administration of the inhalable liquid. The receptacle may be formed as a single manufactured part. The receptacle lid may be separately formed from the same or a different material. In one embodiment the receptacle and the receptacle lid are independently made from a material selected from the group consisting of a polymeric material, a metal (for example, aluminium, nickel) and a metal alloy (for example, stainless steel).

Polymers are particularly suited to large scale manufacturing of the present device and polymeric films described herein by injection moulding, blow moulding and extrusion processes. They may also be suitable for manufacturing the present device on a smaller scale by 3D printing techniques. Further, polymers may be recycled following disposal of the device.

Examples of polymers for use in making the present device and polymeric films described herein may include but are not limited to the following polymers and combinations (including co-extruded polymers) thereof: polyolefins such as polypropylene ('PP'), polyethylene (PE) including low density ('LDPE'), linear low density ('LLDPE') and high density polyethylene ('HDPE'), biaxially orientated polypropylene ('BOPP'), 4-methylpentene, polymethylpentene, polycyclomethylpentene; polymeric phthalates such as polyethylene naphthalates ('PEN'), polyethylene terephthalate ('PET') (also known as ('PETE')), polyethylene terephthalate polyester ('PETP'), polyethylene isophthalate ('PEI'), polybutylene terephthalate ('PBT'), polytrimethylene terephthalate ('PTT'), polycyclohexylenedimethylene terephthalate ('PCT'); fluorinated polymers including polymers fluorinated after manufacture (e.g. fluorination post-moulding), fluorinated ethylene-propylene, chlorotrifluoroethylene ('Kel-F'), polytetrafluoroethylene ('PTFE'); polyesters including cellulose acetate, polyoxymethylene ('POM') and polyesters containing a terephthalate ester group including co-polymers such polyethylene terephthalate glycol co-polyester ('PETG'), polycyclohexylenedimethylene terephthalate glycol modified ('PCTG') and polycyclohexylenedimethylene terephthalate/isophthalic acid ('PCTA'); nylons including amorphous nylon; polyvinyls including polyvinyl alcohol ('PVA') and ethylene vinyl alcohol ('EVOH'); polysulfones including polyethersulfone ('PES'); and natural polymers including starch, cellulose and proteins. Suitable polymers may also include polymers with a moisture vapour transmission rate ('MVTR', also known as water vapour transmission rate 'WVTR') of less than 100 g/m$^2$/24 h, preferably less than 50 g/m$^2$/24 h.

Accordingly, in one embodiment the device is made from one or more polymers wherein the device further comprises an optional internal lining or coating with one or more material(s) selected from the group consisting of polymers (including homopolymers and heteropolymers (also known as co-polymers) and combinations thereof including co-extruded polymers), composites (including nanocomposites such as polymers in combination with clay), metals (including aluminium, nickel and alloys thereof), oxides (including aluminium oxides, silicon oxides), spray coatings, resins (including epoxyphenolic resins and ionomeric resins such as Surlyn®, trademark of DuPont), lacquers and enamels.

In one embodiment the polymer is selected from a polyolefin, a polymeric phthalate, a fluorinated polymer, a polyester, a nylon, a polyvinyl, a polysulfone, a natural polymer and combinations, including co-extruded polymers thereof. In one embodiment the polymer has a MVTR of less than 100 g/m$^2$/24 h, preferably less than 50 g/m$^2$/24 h. In one embodiment the polyolefin is selected from the group consisting of PP, PE, LDPE, LLDPE, HDPE, 4-methylpentene, polymethylpentene polycyclomethylpentene and combinations, including co-extruded polymers, thereof. In one embodiment the polymeric phthalate is selected from the group consisting of PEN, PET, PETP, PEI, PBT, PTT, PCT and combinations, including co-extruded polymers thereof such as BOPP. In one embodiment the fluorinated polymer is selected from Kel-F, PTFE and combinations, including co-extruded polymers thereof. In one embodiment the polyester is selected from the group consisting of cellulose acetate, POM and polyesters containing a terephthalate ester group including PETG, PCTG, PCTA and combinations, including co-extruded polymers, thereof. In one embodiment the nylon is an amorphous nylon. In one embodiment the polyvinyl is selected from PVA, EVOH and combinations, including co-extruded polymers, thereof. In one embodiment the polysulfone is PES. In one embodiment the natural polymer is selected from the group consisting of starch, cellulose, proteins and combinations, including co-extruded polymers, thereof.

In one embodiment the device is made from a single polymer selected from the group consisting of PP, PE, LDPE, LLDPE, HDPE, BOPP, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof. In another embodiment the device is made from two or more polymers selected from the group consisting of PP, PE, LDPE, LLDPE, HDPE, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof. In one embodiment, the device is made from a polymer selected from the group consisting of HDPE, PET and combinations thereof. In one embodiment the device comprises PET.

In embodiments where the receptacle lid or receptacle comprises an integrally formed mouthpiece for delivery of the vapour via the vapour inhalation opening, the shape of the mouthpiece may be any suitable shape for patient use. In one embodiment, the mouthpiece is tapered towards the mouthpiece hole. In one embodiment the cross-sectional shape of the mouthpiece hole is adapted to fit a conventional aerosol or nebuliser face mask.

As the inhalable liquid may be self-administered by a patient using the device, the device may optionally comprise a lanyard and a point for attachment thereto for placement around the patient's wrist or neck. Accordingly, in one embodiment the device comprises a lanyard and a point for attachment thereto.

Example 1

Figure 1:
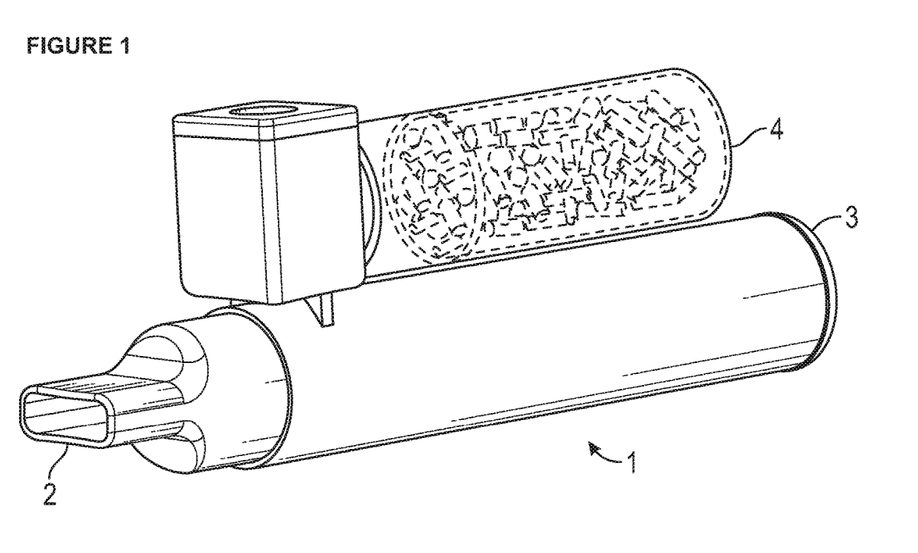
FIG. 1 shows a prior art inhaler device, referred to as the Green Whistle™ inhaler device (Medical Developments International Limited) that is currently used to administer methoxyflurane.

FIG. 1 shows the prior art Green Whistle™ inhaler device (1) (Medical Developments International Limited) which is currently used in Australia for the delivery of Penthrox®/™ (methoxyflurane) as an analgesic (1.5 mL or 3 mL, storage brown glass vial container with screw cap). When required for use, the delivery dose of methoxyflurane is poured into the base end (3) of the device. After the dose is poured into the base end for delivery onto the evaporative means (not shown), the methoxyflurane evaporates so that the patient can self-administer the analgesic by inhaling the air/vapour mix through the mouthpiece (2). Provided that the patient continues to breathe through the mouthpiece, any exhaled air/vapour mix will exit the device via the externally fitted chamber containing activated carbon 'AC-chamber' (4).

Example 2

Figure 2A:
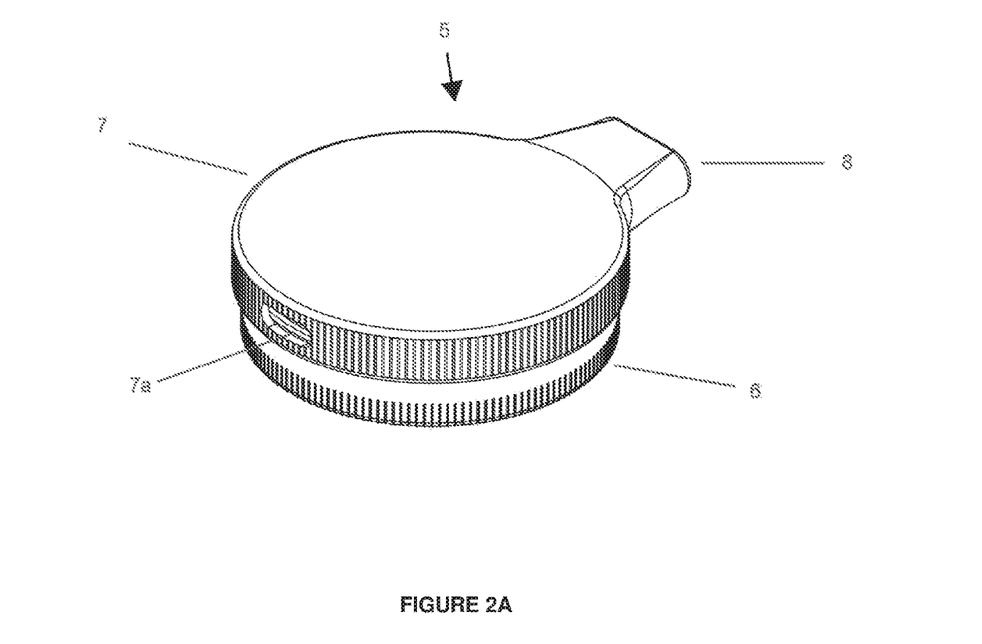
Figure 2B:
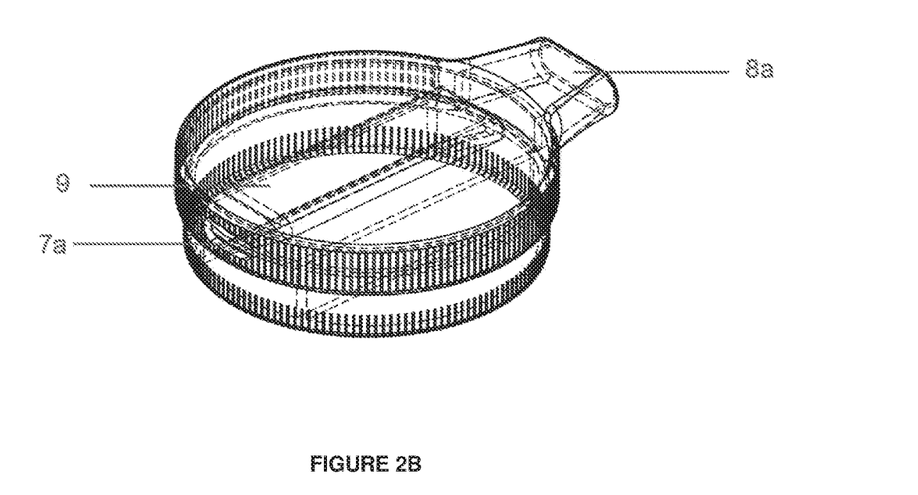
Figures 3, 3A:
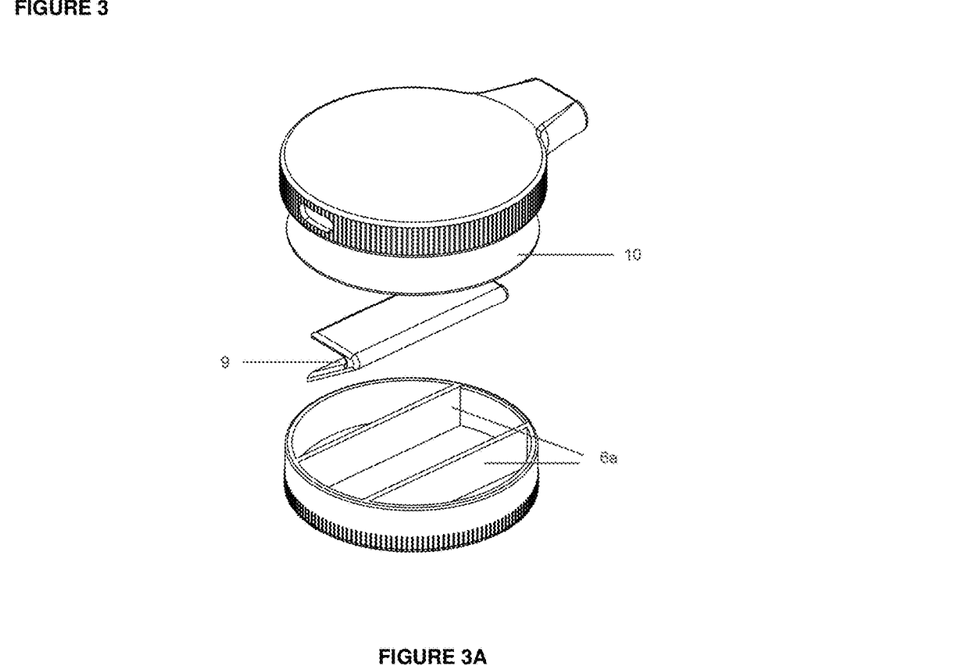
FIG. 3 shows an exploded view of the inhaler device of FIG. 2A to better illustrate some internal components.
Figure 3B:
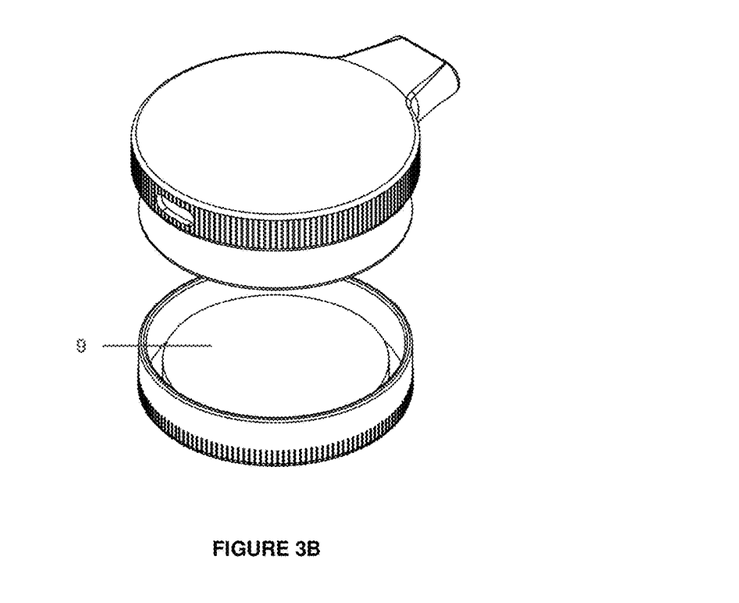
Figures 4, 4A:
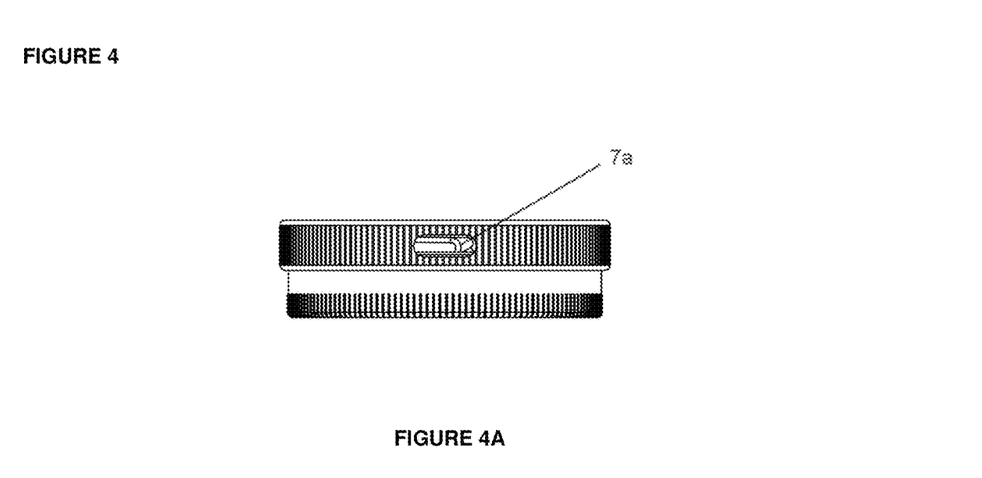
Figure 4B:
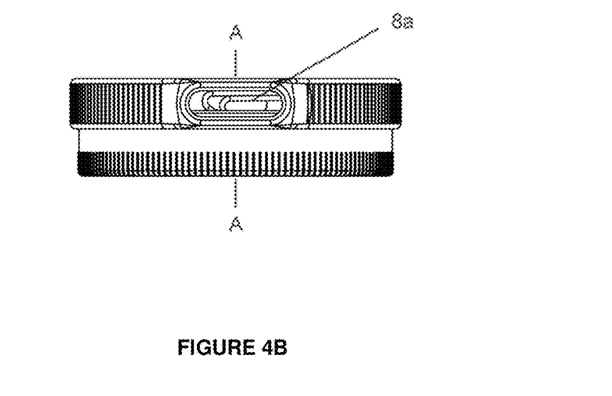
Figure 4C:
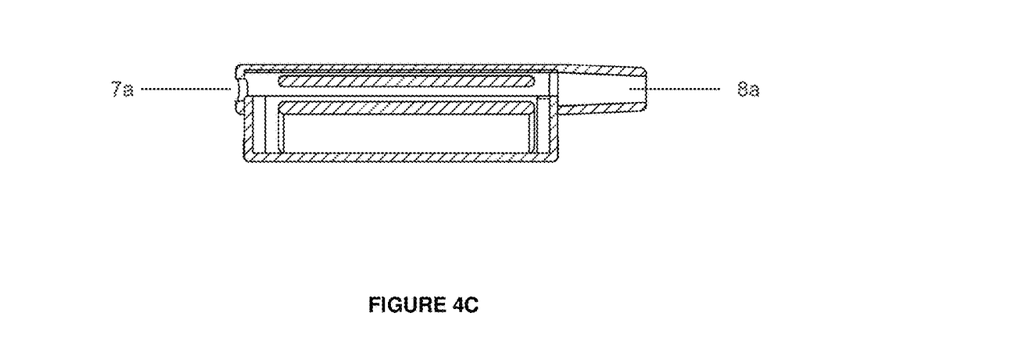
Figure 5A:
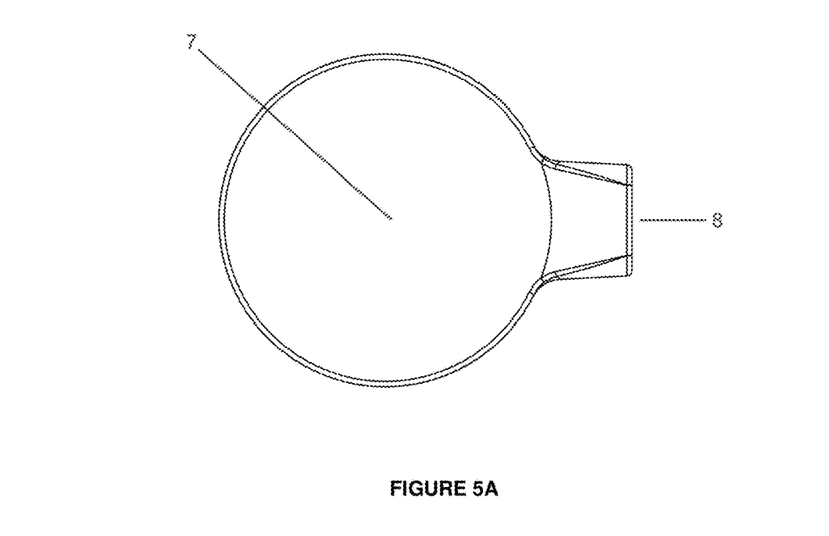
Figure 5B:
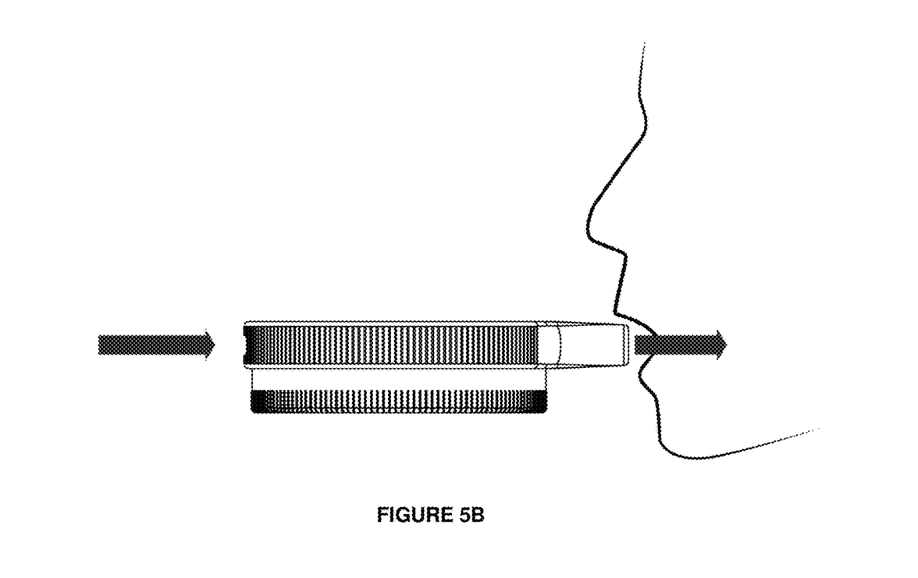

FIG. 2A shows an inhaler device (5) according to an embodiment of the invention. The inhaler device has a puck-shaped body and comprises a receptacle (6) and a receptacle lid (7) with an air inlet hole (7a) and an integrally formed and partially tapered mouthpiece (8). A top view of the device is shown in FIG. 5A to better illustrate the shape of the lid and mouthpiece. The vapour inhalation hole (8a) in the mouthpiece is shown by the broken line drawing in FIG. 2B. Also shown is the internally stored passive evaporation support material which is pre-loaded with an inhalable liquid (9) such as methoxyflurane. In storage mode, the inhaler device functions as a sealed storage container for the inhalable liquid and its vapour so that it is primed and ready for immediate delivery of the drug in vapour form to the patient upon opening. The exploded view presented in FIG. 3 shows the passive evaporation support material in a folded arrangement. To prevent movement of the passive evaporation support material upon storage and/or use, the receptacle also comprises positioning means (6a). The receptacle lid also comprises a wad insert (10). When the lid is opened, an air flow pathway is formed through the vapour chamber air inlet opening and vapour inhalation opening. FIG. 4A shows the air flow pathway from the air inlet hole (7a) end and FIG. 4B shows the air flow pathway from the vapour inhalation hole (8a) end. FIG. 4C is a cross-sectional view to provide a side perspective of the air flow pathway through the vapour chamber from the air inlet hole to the vapour inhalation hole. The device in use is further illustrated in FIG. 5B which shows the direction of the air/vapour flow upon inhalation by a patient.

Example 3

The ability of an inhaler device to delivery methoxyflurane may be tested using a breath simulator system such as a pulmonary waveform generator system.

The delivery of methoxyflurane (% concentration) by the Green Whistle device with the external AC chamber attached and a Prototype device (FIG. 2) according to the invention was measured using a pulmonary waveform generator system. The Prototype device was manufactured as a rapid prototype using a HDPE equivalent material.

Both devices were tested as follows. The pulmonary waveform generator was set to "Adult" flow conditions (14 breaths per minute) and the concentration logging software and Datex Sensor commenced. For each test, the polypropylene wick was pre-loaded with methoxyflurane (3 mL) to be delivered and the mouthpiece end of the device then inserted into the opening of the pulmonary waveform generator. Concentration logging was commenced for the first minute for the first breaths concentration and then for the next 20 minutes for steady state testing.

Figure 6:
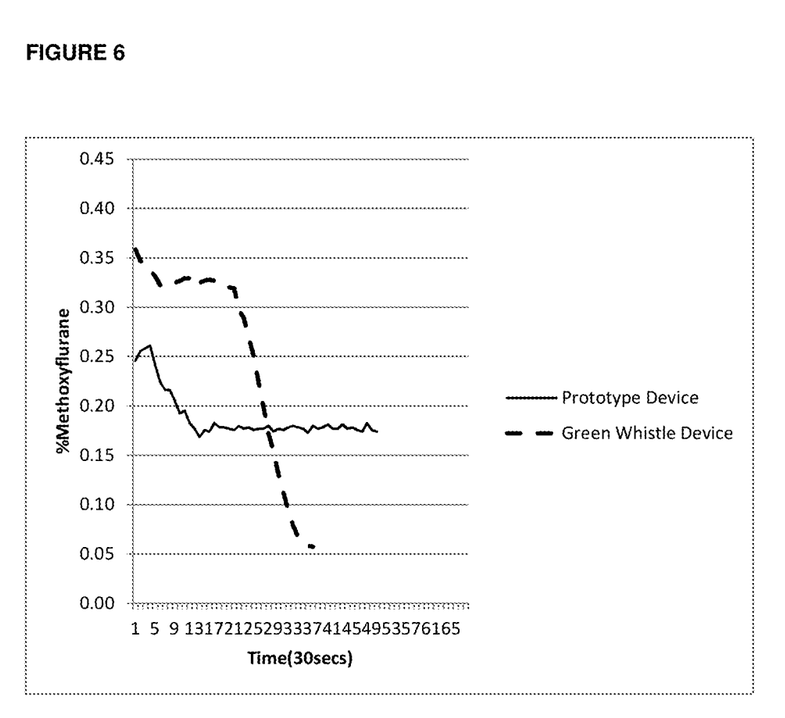
FIG. 6 shows the comparative concentrations of methoxyflurane delivered by a device (FIG. 2A) according to an embodiment of the invention and the prior art Green Whistle inhaler (FIG. 1).

The results are presented in FIG. 6. In both cases, the devices delivered methoxyflurane. While the Green Whistle device initially delivered methoxyflurane at a higher level, the Prototype device was shown to maintain a steady state level over a longer period of time. Accordingly, the Prototype device was shown to deliver a lower concentration of methoxyflurane for a longer duration. In contrast, the Green Whistle device was shown to deliver methoxyflurane at a higher steady state level for a shorter duration initially which was then followed by a rapid reduction below the steady state concentration of methoxyflurane achieved by the Prototype device.

Throughout this specification and the claims which follow, unless the context requires otherwise, the word "comprise" and variations thereof such as "comprises" and "comprising", will be understood to imply the inclusion of a stated integer or step or group of integers or steps but not to the exclusion of any other integer or step or group of integers or steps.

The reference in this specification to any prior publication or information derived from it, or to any matter which is known is not and should not be taken as an acknowledgement or admission or any form of suggestion that prior publication, or information derived from it, or known matter, forms part of the common general knowledge in the field of endeavour to which this specification relates.

The invention claimed is:

1. An inhaler device for the storage and delivery of an inhalable liquid to a patient, said inhaler device comprising a puck-shaped body wherein the puck-shaped body comprises:
   (1) a receptacle comprising a passive evaporation support material pre-loaded with the inhalable liquid;
   (2) a receptacle lid;
   (3) at least one air inlet opening; and
   (4) at least one vapour inhalation opening;
wherein the at least one air inlet and at least one vapour inhalation openings are in a closed position when the receptacle lid is closed for storing the inhalable liquid and further wherein as the inhalable liquid forms a vapour upon storage, the puck-shaped body forms a vapour chamber such that the stored vapour is available for direct administration to a patient when the receptacle lid is opened to provide an air/vapour pathway through the vapour chamber via the at least one air inlet and at least one vapour inhalation openings.

2. The inhaler device according to claim 1 wherein the puck-shaped body consists only of:
   (1) the receptacle comprising the passive evaporation support material pre-loaded with the inhalable liquid;
   (2) the receptacle lid;
   (3) the at least one air inlet opening; and
   the at least one vapour inhalation opening;
wherein the at least one air inlet and at least one vapour inhalation openings are in the closed position when the receptacle lid is closed for storing the inhalable liquid and further wherein as the inhalable liquid forms a vapour upon storage, the puck-shaped body forms the vapour chamber such that the stored vapour is available for direct administration to a patient when the receptacle lid is opened to provide the air/vapour pathway through the vapour chamber via the at least one air inlet and at least one vapour inhalation openings.

3. The inhaler device according to claim 1 wherein the receptacle lid is opened by popping, upward pulling, twisting, turning, rotating or unscrewing the receptacle lid relative to the receptacle.

4. The inhaler device according to claim 1 wherein the receptacle lid is detachably fastened to sealingly engage with the receptacle.

5. The inhaler device according to claim 1 wherein the receptacle lid is rotatably openable.

6. The inhaler device according to claim 1 wherein the at least one air inlet opening and the at least one vapour inhalation opening are formed in the receptacle lid.

7. The inhaler device according to claim 1 wherein the at least one air inlet opening and the at least one vapour inhalation opening are formed in both the receptacle lid and the receptacle to provide an air flow pathway through the inhaler device when the receptacle lid is adjustably opened to adjustably control the air flow pathway by partially or fully aligning openings in the receptacle lid with openings in the receptacle to deliver the vapour to the patient when the patient inhales.

8. The inhaler device according to claim 1 wherein the receptacle lid is flat.

9. The inhaler device according to claim 1 wherein the receptacle lid comprises grips to assist the patient with opening the receptacle lid.

10. The inhaler device according to claim 1 wherein the receptacle lid comprises a wad insert.

11. The inhaler device according to claim 1 wherein the receptacle lid comprises an integrally formed mouthpiece for delivery of the vapour via the at least one vapour inhalation opening.

12. The inhaler device according to claim 11 wherein the mouthpiece is adapted to fit an aerosol or nebuliser face mask.

13. The inhaler device according to claim 1 wherein the inhalable liquid is methoxyflurane for use as an analgesic.

14. The inhaler device according to claim 13 wherein the methoxyflurane is for delivery to a patient in a delivery dose of less than 15 mL.

15. The inhaler device according to claim 1 wherein the passive evaporation support material is a polypropylene wicking felt.

16. The inhaler device according to claim 1 wherein the inhaler device is manufactured from a material selected from the group consisting of polymers, composites, metals and combinations thereof.

17. The inhaler device according to claim 1 wherein the inhaler device is manufactured from one or more polymers and comprises an internal lining or coating of one or more materials selected from the group consisting of polymers including homopolymers and heteropolymers and combinations (including co-extruded polymers) thereof; polymer composites including nanocomposites; oxides including aluminium oxides; silicon oxides; spray coatings; resins including epoxyphenolic resins and ionomeric resins; lacquers; and enamels.

18. The inhaler device according to claim 17 wherein the polymers of the internal lining or coating is selected from the group consisting of a polyolefin, a polymeric phthalate, a fluorinated polymer, a polyester, a nylon, a polyvinyl, a polysulfone, a natural polymer and combinations, including co-extruded polymers thereof.

19. The inhaler device according to claim 1 wherein the device is manufactured from one or more polymers selected from the high density polyethylene (HDPE), polyethylene terephthalate (PET) and combinations thereof.

* * * * *